US 6,489,781 B1

(12) United States Patent
Kliman et al.

(10) Patent No.: US 6,489,781 B1
(45) Date of Patent: Dec. 3, 2002

(54) METHOD AND SYSTEM FOR DETECTING CORE FAULTS

(75) Inventors: Gerald Burt Kliman, Niskayuna, NY (US); Manoj Ramprasad Shah, Latham, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/681,802

(22) Filed: Jun. 7, 2001

(51) Int. Cl.$^7$ ............................................. G01R 31/06
(52) U.S. Cl. ....................... 324/545; 324/529
(58) Field of Search .................... 324/545, 772, 324/240, 242, 243, 529; 340/686.3

(56) References Cited

U.S. PATENT DOCUMENTS

| 4,230,961 A | * 10/1980 | Calfo et al. ................. 324/545 |
| 4,996,486 A | 2/1991 | Posedel ....................... 324/545 |
| 5,990,688 A | 11/1999 | Bourgeois et al. .......... 324/545 |

FOREIGN PATENT DOCUMENTS

| GB | 2 044 936 A | 8/1979 |

OTHER PUBLICATIONS

C. Rickson, et al, "Electrical Machine Core Imperfection Detection", IEEE Proceedings B (Electric Power Applications) vol. 133, No. 3, pp. 181–189.

JW Shelton, et al, "Introduction and Qualification of Digital Electromagnetic Core Imperfection Detector (EL CID) Test Equipment and Associated Robotic Delivery and Inspection Systems", Proceedings of the American Power Conference, vol. 56–II, 1994, pp. 1735–1742.

JW Shelton, et al, "A Comparative Analysis of Turbogenerator Core Inspection Techniques", Proceedings of the American Power Conference, vol. 47, pp. 643–650.

DJ Cadwell, et al, "Fast Gen III", The Proceedings of the American Power Conference, vol. 58–11, 1996, pp. 1249–1255.

J. Sutton, "Theory of Electromagnetic Testing of Laminated Stator Cores", Insight, vol. 36, No. 4, Apr. 1994, pp. 246–251.

U.S. patent application Ser. No. 09/575,715, Electronically Filed on Jul. 28, 2000 by Gerald B. Kliman, et al, Entitled "Method and System for Detecting Core Faults".

* cited by examiner

*Primary Examiner*—Christine K. Oda
(74) *Attorney, Agent, or Firm*—Ann M. Agosti; Jill M. Breedlove

(57) ABSTRACT

A method for detecting core faults includes: positioning a magnetic yoke near at least one tooth of the core, the magnetic yoke being wound by a winding and comprising two core-facing surfaces and at least one flux sensor situated on at least one of the two core-facing surfaces; supplying current to the winding to inject magnetic flux into the at least one tooth; using the at least one flux sensor to measure a signal resulting from the injected magnetic flux; and using the measured signal to detect variations in flux on the at least one core-facing surface representative of core faults. A system includes: at least one magnetic yoke for being positioned near at least one tooth of the core and being wound by a winding and comprising two core-facing surfaces; and at least one flux sensor situated on at least one of the two core-facing surfaces.

20 Claims, 2 Drawing Sheets

METHOD AND SYSTEM FOR DETECTING CORE FAULTS

BACKGROUND OF THE INVENTION

The invention relates generally to detecting core faults and more particularly to testing laminated cores of electric machines for interlamination short circuits.

A conventional large generator lamination segment includes a back iron, teeth and slots. Lamination segments (each about 254 microns to about 508 microns thick) are formed into a magnetic core by stacking. Typically a plurality of lamination segments (eighteen lamination segments each being twenty degrees, for one example) are used to form a complete first lamination with the next plurality of lamination segments forming a complete second lamination on top of and offset from the lamination segments in the first lamination. The stacking continues until formation of a short stack of about 2.54 centimeters to about 10.16 centimeters thick. A plurality of short stacks are further joined and/or clamped by bolts and/or other mechanical devices to form a stator core. A typical large generator stator core has a diameter ranging from about 1 meter to about 3 meters and a length ranging from about 1 meter to about 10 meters.

Laminated stator cores are tested for interlamination shorts during manufacture and during maintenance or service procedures. Core faults, such as faults caused by short circuited laminations, in large electric machines can be highly destructive.

As described in commonly assigned Kliman et al., U.S. patent application Ser. No. 09/575,715, filed Jul. 28, 2000 and allowed Feb. 25, 2002, core faults may be detected by positioning a magnetic yoke wound by a winding near at least one tooth of the core; supplying current to the winding to inject magnetic flux into the at least one tooth; measuring at least one signal resulting from the injected magnetic flux; and using the measured signal to detect core faults. When a small portion of the core is excited, if the laminations are well insulated from each other, the flux response to the excitation will be primarily due to the permeable core material as modified by normal hysterisis losses and eddy currents in the laminations. However, if faults exist anywhere in the excited region, circulating currents will be induced which will alter the magnitude and phase of the response. Such altered phases or magnitudes can be used as a core condition indicator when used to compare one region of the core with another region of the core or to trend a single region over time. Additionally, analysis of the signal distribution for normal conditions and known fault conditions can be used to interpret measured signals in order to estimate core condition.

U.S. patent application Ser. No. 09/575,715 has several advantages as compared to prior embodiments. For example, short stacks of laminations can be tested individually while stacking during core fabrication and/or during core servicing so that, if a fault is located, remedial measures can be taken immediately on the affected lamination, and, if no fault is located, additional stacks can be formed and tested. In contrast, in prior embodiments, if a fault is later located in the middle of a completed core, a substantial portion of the core had to be un-stacked to gain access to the fault.

When the thickness of the magnetic yoke in U.S. patent application Ser. No. 09/575,715 exceeds the thickness of about two or three core laminations, sensitivity and selectivity are reduced since the magnetic yoke itself will influence the losses measured along the winding. Physical and practical constraints limit minimum yoke thicknesses however. Another factor that influences sensitivity is the distance between the magnetic yoke and the core laminations. About 50–75 micrometers of lamination stagger typically result from punching tolerances and assembly variability when fabricating laminated cores. In machines which function as generators, lamination core stagger is typically filled in and covered up by layers of thick paint. Such paint would further increase the effective gap between the magnetic yoke and the core.

It would be desirable to have a core fault detection method with increased sensitivity.

SUMMARY OF INVENTION

Briefly, in accordance with one embodiment of the present invention, a method for detecting core faults comprises (a) positioning a magnetic yoke near at least one tooth of the core, the magnetic yoke being wound by a winding and comprising two core-facing surfaces and at least one flux sensor situated on at least one of the two core-facing surfaces; (b) supplying current to the winding to inject magnetic flux into the at least one tooth of the core; (c) using the at least one flux sensor to measure a signal resulting from the injected magnetic flux; and (d) using the measured signal to detect variations in flux on the at least one core-facing surface representative of core faults.

In accordance with another embodiment of the present invention, a system for detecting core faults comprises at least one magnetic yoke for being positioned near at least one tooth of the core, the at least one magnetic yoke being wound by a winding and comprising two core-facing surfaces and at least one flux sensor situated on at least one of the core-facing surfaces.

BRIEF DESCRIPTION OF DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
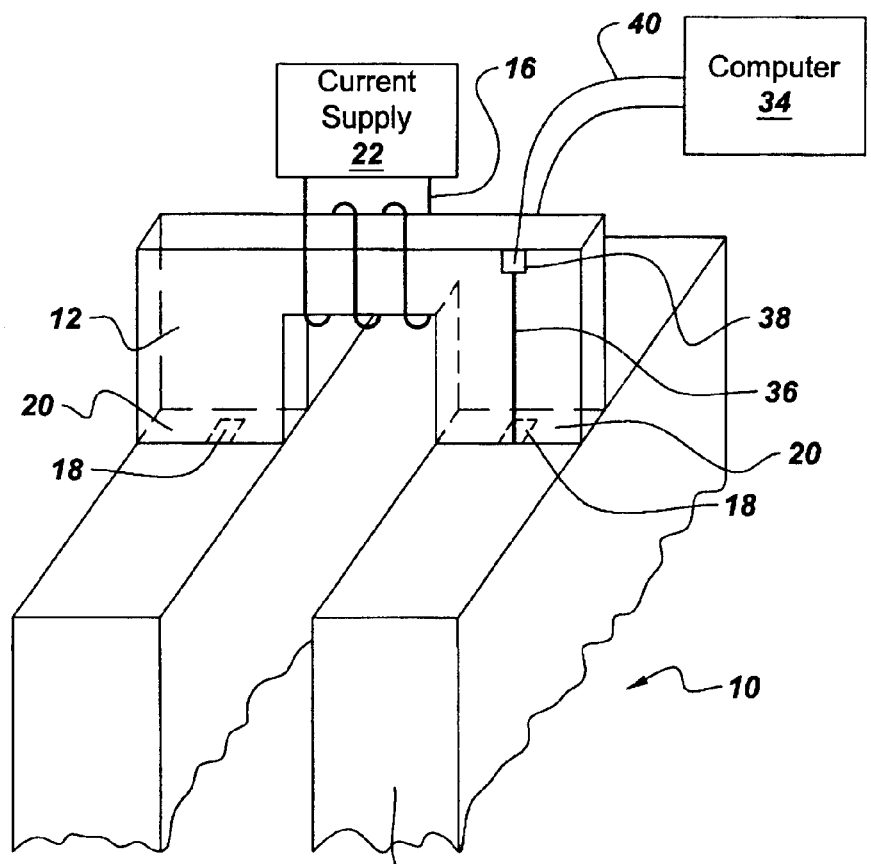
FIG. 1 is a perspective view of a magnetic yoke for sensing core faults in accordance with one embodiment of the present invention.

FIG. 1 is a perspective view of a magnetic yoke 12 for sensing core 10 faults in accordance with one embodiment of the present invention wherein a method for detecting core 10 faults comprises: (a) positioning a magnetic yoke 12 near at least one tooth 14 of the core, the magnetic yoke being wound by a winding 16 and comprising two core-facing surfaces 20 and at least one flux sensor 18 situated on at least one of the two core-facing surfaces; (b) supplying current to the winding to inject magnetic flux into the at least one tooth of the core; (c) using the at least one flux sensor to measure a signal resulting from the injected magnetic flux; and (d) using the measured signal to detect variations in flux on the at least one core-facing surface representative of core faults. The word "near" is meant to include actual physical contact or close enough proximity (typically less than or equal to about 254 micrometers distance, for example) so that the resulting signal has sufficient resolution for fault detection.

More specifically, in the embodiment of FIG. 1, the magnetic yoke is positioned near two teeth, and, even more specifically is a U-shaped (meaning U-shaped or C-shaped) yoke positioned near two adjacent teeth. Although adjacent teeth are shown in FIG. 1, the two teeth may have another tooth or multiple teeth therebetween. Magnetic yoke 12 may comprise a laminated, tape-wound, or molded (bonded iron or steel particle composite) yoke. For laminated or tape-wound yokes, it is useful (but not required) to have the direction of lamination or winding of the yoke be the same direction as the direction of lamination of core 10. It is useful to have the thickness of the yoke be in the range of about 1 millimeter to about 15 millimeters.

Flux sensor 18 comprises a sensor capable of being mounted on a core-facing surface of magnetic yoke 12. Thin film type sensors such as planar flux coils and Hall effect devices, for example, are considered to be particularly suitable for mounting on magnetic yokes.

Figure 2:
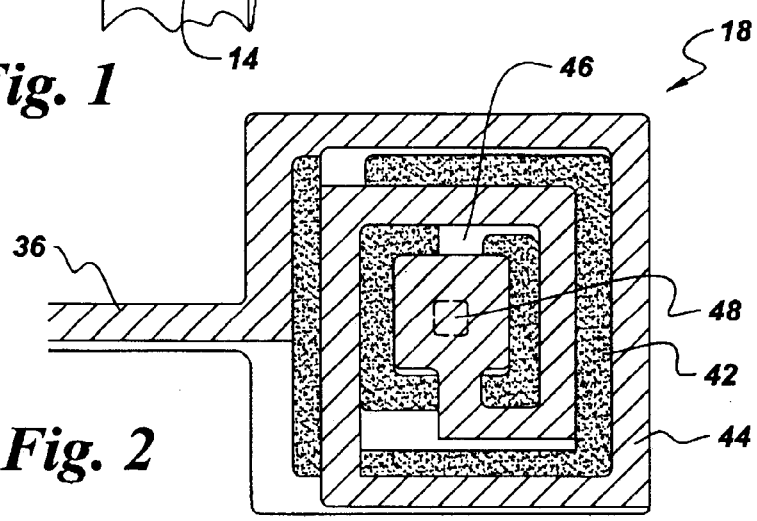
FIGS. 2 and 3 are respective front and sectional side views of a typical flux sensor for use with the magnetic yoke of FIG. 1 in accordance with a more specific embodiment of the present invention.
Figure 3:
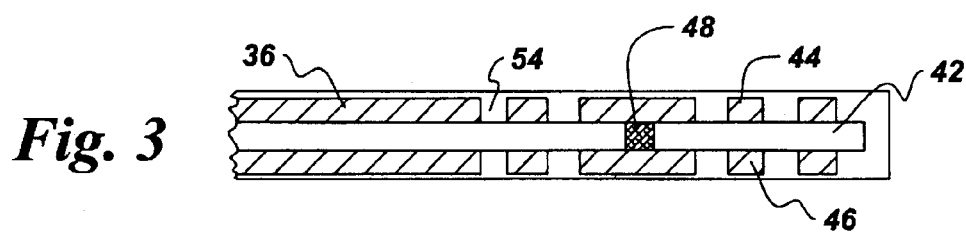

FIGS. 2 and 3 are respective front and sectional side views of a flux sensor for use with the magnetic yoke of FIG. 1 in accordance with an embodiment wherein flux sensor 18 comprises a (meaning at least one) planar coil 44. An advantage of using a planar coil is that such coils can be fabricated as thin films. In one example, a coil having several turns has a thickness of about 0.0762 millimeters with each side of the coil being about 0.7620 millimeters long.

In one embodiment, flux sensor 18 further comprises a dielectric layer 42, planar coil 44 is situated on a dielectric layer 42, and flux sensor 18 further comprises a protective layer 54 overlying the planar coil and the dielectric layer. Dielectric layer 42 may comprise any non-electrically conductive material with sufficient structural integrity to withstand the fabrication and operating environment of the flux sensor. In one example, dielectric layer 42 comprises a polyimide such as KAPTON™ polyimide (KAPTON is a trademark of DuPont Co.) having a thickness of about 25 micrometers.

Planar coil 44 can be fabricated on dielectric layer 42 by standard metallization and patterning techniques. In one example, the planar coil is applied by metallizing dielectric layer 42 with a conventional printed circuit board or chip interconnection material such as copper and patterning the metallization using conventional techniques.

Protective layer 54 may comprise a dielectric material such as MYLAR™ polyester film (MYLAR is a trademark of DuPont Co.) having a thickness of about 25 micrometers, for example.

FIGS. 2 and 3 further illustrate an optional embodiment wherein planar coil 44 comprises a first planar coil and wherein flux sensor 18 further comprises a second planar coil 46 and a conductive via 48 extending through the dielectric layer to electrically couple the first and second planar coils. Second planar coil 46 may be formed in a similar manner as discussed with respect to first coil 44. Conductive via 48 may be provided by forming a hole in the dielectric layer by mechanical punching or laser ablation, for example, and by metallizing the hole prior to application of the first and second planar coils or simultaneously with the application of a first or second planar coil.

Planar coil 18 may be coupled by coupler 36 to a connector terminal 38 (FIG. 1) by any appropriate technique. In one embodiment, for example, coupler 36 is patterned on the same dielectric film 42 as planar coil 44 and extends to a connector terminal 38 situated on magnetic yoke 12. In this embodiment, connector terminal 38 may be situated in any convenient location on the yoke with the location in FIG. 1 being for purposes of example only. Leads 40 can then be coupled to connector terminal 38 for transmitting flux signals to computer 34.

Figure 4:
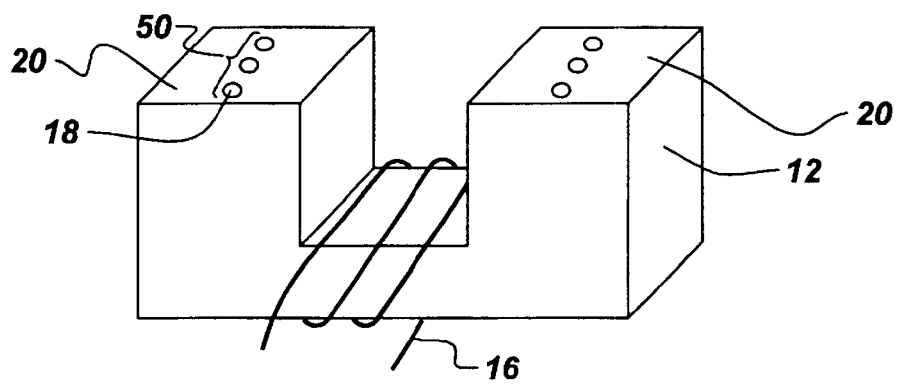
FIG. 4 is a perspective view of a magnetic yoke in accordance with another embodiment of the present invention.
Figure 5:
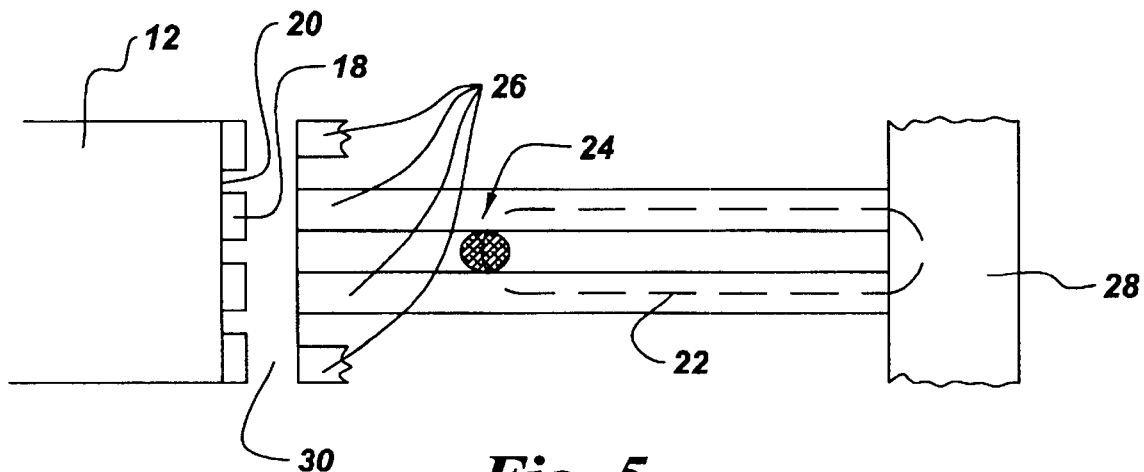
FIG. 5 is a sectional side view of the embodiment of FIG. 4.

FIG. 4 is a perspective view of a magnetic yoke in accordance with another embodiment of the present invention wherein an array 50 (meaning "a plurality") of flux sensors is situated on one core-facing surface or both core-facing surfaces of the magnetic yoke, and FIG. 5 is a sectional side view of the embodiment of FIG. 4 which illustrates a current loop 22 which results from the presence of a core fault 24 between two laminations 26. Typically the current loop will form between the fault and a key bar 28 and along the affected laminations. The resulting current creates additional losses as well as a shift in the magnetic potential or field of the laminations. Thus, the local field in the gap 30 between the magnetic yoke 12 and a tooth will be disturbed in the vicinity of the affected laminations. By scanning the flux sensor voltages, a pattern of gap flux density can be recorded. Anomalies in the pattern represent a core fault indication with the location of the flux sensors at the anomaly points indicating which laminations are affected by the fault.

Figure 6:
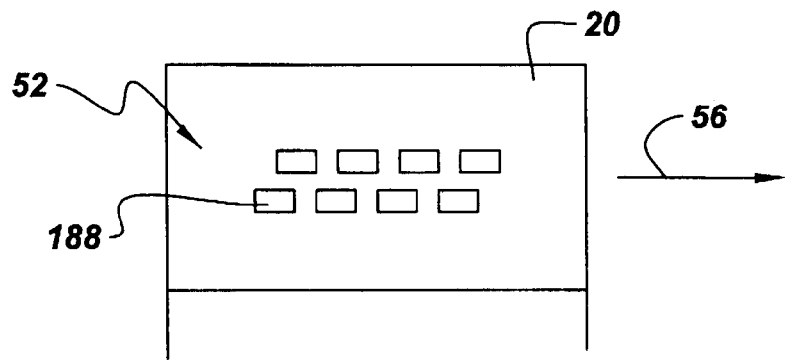
FIG. 6 is a front view of a magnetic yoke in accordance with another embodiment of the present invention.

FIG. 6 is a front view of a magnetic yoke in accordance with another embodiment of the present invention including a staggered array 52 of flux sensors. Typically laminations are about 0.3556 millimeters. If laminations (shown as laminations 26 in FIG. 5) are thinner than the perimeter dimensions of at least one flux sensor, the identification of the precise location of a fault (that is, the selectivity) can become more difficult. Selectivity can be improved, for example, as shown in the embodiment of FIG. 6, by arranging two or ore rows of offset flux sensors and moving the yoke in the direction of arrow 56.

Regardless of which of the one or more flux sensor embodiments is selected, the steps of supplying current, measuring the resulting signal, and using the measured signal to detect core faults are typically repeated such that a plurality of measurements are used to detect core faults. The measurements can be performed, for example, by axially moving the magnetic yoke relative to the at least one tooth. Preferably, measurements are made until all regions of the core have been tested.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A method for detecting core faults comprising:
   (a) positioning a magnetic yoke near at least one tooth of the core, the magnetic yoke being wound by a winding and comprising two core-facing surfaces and at least one flux sensor situated on at least one of the two core-facing surfaces;
   (b) supplying current to the winding to inject magnetic flux into the at least one tooth of the core;

(c) using the at least one flux sensor to measure a signal resulting from the injected magnetic flux; and (d) using the measured signal to detect variations in flux on the at least one core-facing surface representative of core faults.

2. The method of claim 1 further comprising repeating (a)–(c) and using the plurality of resulting measured signals to detect core faults in (d).

3. The method of claim 2 wherein, when repeating (a)–(c), positioning comprises axially moving the magnetic yoke relative to the at least one tooth.

4. The method of claim 1 wherein the at least one flux sensor comprises at least one planar coil.

5. The method of claim 4 wherein the at least one flux sensor further comprises a dielectric layer, wherein the at least one planar coil is situated on the dielectric layer, and wherein the at least one flux sensor further comprises a protective layer overlying the at least one planar coil and the dielectric layer.

6. The method of claim 1 wherein the at least one flux sensor comprises a plurality of flux sensors on each of the two core-facing surfaces.

7. A method for detecting core faults comprising:

(a) positioning a magnetic yoke near two teeth of the core, the magnetic yoke being wound by a winding and comprising two core-facing surfaces and at least two flux sensors with at least one of the at least two flux sensors being situated on each of the two core-facing surfaces;

(b) supplying current to the winding to inject magnetic flux into the two teeth of the core;

(c) using the at least two flux sensors to measure signals resulting from the injected magnetic flux; and (d) using the measured signals to detect variations in flux on the two core-facing surfaces representative of core faults.

8. The method of claim 7 wherein each of the at least two flux sensors comprises at least one planar coil.

9. The method of claim 8 wherein the at least two flux sensors comprise a plurality of flux sensors on each of the two core-facing surfaces.

10. A system for detecting core faults comprising: at least one magnetic yoke for being positioned near at least one tooth of the core, the at least one magnetic yoke being wound by a winding and comprising two core-facing surfaces and at least one flux sensor situated on at least one of the two core-facing surfaces.

11. The system of claim 10 further comprising a current supply for supplying current to the winding to inject magnetic flux into the at least one tooth of the core, and a computer for using signals from the flux sensors to detect core faults.

12. The system of claim 10 wherein the at least one flux sensor comprises at least one planar coil.

13. The system of claim 12 wherein the at least one flux sensor further comprises a dielectric layer, wherein the at least one planar coil is situated on the dielectric layer, and wherein the at least one flux sensor further comprises a protective layer overlying the at least one planar coil and the dielectric layer.

14. The system of claim 13 wherein the at least one planar coil comprises a first planar coil, and wherein the at least one flux sensor further comprises a second planar coil and a conductive via extending through the dielectric layer to electrically couple the first and second planar coils.

15. The system of claim 13 wherein the at least one flux sensor comprises an array of flux sensors on each of the two core-facing surfaces.

16. The system of claim 10 wherein the at least one flux sensor comprises an array of flux sensors on each of the two core-facing surfaces.

17. The system of claim 10 wherein the at least one flux sensor comprises a staggered array of flux sensors.

18. A system for detecting core faults comprising: at least one magnetic yoke for being positioned near at least one tooth of the core, the at least one magnetic yoke being wound by a winding and comprising two core-facing surfaces and at least two flux sensors each comprising at least one planar coil situated on a respective one of the two core-facing surfaces.

19. The system of claim 18 wherein each of the at least two flux sensors further comprises a dielectric layer, wherein the at least one planar coil is situated on the dielectric layer, and wherein the at least one flux sensor further comprises a protective layer overlying the at least one planar coil and the dielectric layer.

20. The system of claim 18 wherein the at least one planar coil comprises a first planar coil, and wherein each of the at least two flux sensors further comprises a second planar coil and a conductive via extending through the dielectric layer to electrically couple the first and second planar coils.

* * * * *